United States Patent
Lechner et al.

(10) Patent No.: US 11,564,876 B2
(45) Date of Patent: *Jan. 31, 2023

(54) METHOD FOR DYEING KERATINOUS MATERIAL, COMPRISING THE USE OF AN ORGANOSILICON COMPOUND, A SILICONE POLYMER AND A DYEING COMPOUND

(71) Applicant: Henkel AG & Co. KGaA, Duesseldorf (DE)

(72) Inventors: Torsten Lechner, Langenfeld (DE); Juergen Schoepgens, Schwalmtal (DE); Marc Nowottny, Moenchengladbach (DE); Gabriele Weser, Neuss (DE); Ulrike Schumacher, Duesseldorf (DE); Claudia Kolonko, Remscheid (DE); Caroline Kriener, Duesseldorf (DE); Carsten Mathiaszyk, Essen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/267,655

(22) PCT Filed: Aug. 7, 2019

(86) PCT No.: PCT/EP2019/071197
§ 371 (c)(1),
(2) Date: Feb. 10, 2021

(87) PCT Pub. No.: WO2020/035362
PCT Pub. Date: Feb. 20, 2020

(65) Prior Publication Data
US 2021/0154121 A1 May 27, 2021

(30) Foreign Application Priority Data
Aug. 16, 2018 (DE) ...................... 10 2018 213 816.8

(51) Int. Cl.
*A61Q 5/10* (2006.01)
*A61K 8/58* (2006.01)
*A61K 8/898* (2006.01)

(52) U.S. Cl.
CPC .............. *A61K 8/585* (2013.01); *A61K 8/898* (2013.01); *A61Q 5/10* (2013.01); A61K 2800/43 (2013.01); A61K 2800/805 (2013.01); A61K 2800/884 (2013.01)

(58) Field of Classification Search
CPC .... A61Q 5/10; A61Q 5/065; A61K 2800/884; A61K 2800/43; A61K 8/25; A61K 2800/432; A61K 8/89; A61K 8/585; A61K 8/898
USPC ........................................................... 8/405
See application file for complete search history.

(56) References Cited

U.S. PATENT DOCUMENTS

| | | | |
|---|---|---|---|
| 7,806,941 B2 | 10/2010 | Brun et al. | |
| 2010/0083446 A1* | 4/2010 | Brun | A61K 8/891 8/405 |
| 2010/0112019 A1 | 5/2010 | Thevenet | |
| 2014/0261516 A1* | 9/2014 | Schulze zur Wiesche | A61K 8/39 424/70.2 |
| 2014/0314696 A1 | 10/2014 | Kergosien et al. | |
| 2015/0080338 A1* | 3/2015 | Lorant | A61Q 19/00 514/63 |
| 2018/0055751 A1 | 3/2018 | Gevgilili et al. | |

FOREIGN PATENT DOCUMENTS

| | | |
|---|---|---|
| EP | 2168633 A2 | 3/2010 |
| WO | 2018/115059 A1 | 6/2018 |
| WO | 2018/187246 A1 | 10/2018 |

OTHER PUBLICATIONS

EPO, International Search Report issued in International Application No. PCT/EP2019/071197, dated Nov. 14, 2019.
Anonymous: "Semi-Permanent Hair Colourant", Apr. 2016, Database GNPD [Online] Mintel; XP055638513.

* cited by examiner

*Primary Examiner* — Eisa B Elhilo
(74) *Attorney, Agent, or Firm* — Lorenz & Kopf, LLP

(57) ABSTRACT

The subject of the present disclosure is a process for dyeing keratinous material, in particular human hair. In one example, the process includes applying an agent (a) to the keratinous material. The agent (a) contains at least one organic silicon compound from the group of silanes with one, two or three silicon atoms. The agent (a) further contains at least one silicone polymer. An agent (b) is applied to the keratinous material. The agent (b) contains at least one pigment.

10 Claims, No Drawings

METHOD FOR DYEING KERATINOUS MATERIAL, COMPRISING THE USE OF AN ORGANOSILICON COMPOUND, A SILICONE POLYMER AND A DYEING COMPOUND

CROSS-REFERENCE TO RELATED APPLICATION

This application is a U.S. National-Stage entry under 35 U.S.C. § 371 based on International Application No. PCT/EP2019/071197, filed Aug. 7, 2019, which was published under PCT Article 21(2) and which claims priority to German Application No. 10 2018 213 816.8, filed Aug. 16, 2018, which are all hereby incorporated in their entirety by reference.

TECHNICAL FIELD

The subject of the present application is a process for dyeing keratinous material, in particular human hair, which comprises the application of at least two different agents (a) and (b). The agent (a) contains at least one organic silicon compound from the group of silanes with one, two or three silicon atoms and furthermore at least one silicone polymer. The agent (b) contains at least one pigment.

The second subject-matter of this application is a multi-component packaging unit (kit-of-parts) for coloring keratinous material, in particular human hair, which comprises the agents (a) and (b) separately packaged in two different containers.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

EP 2168633 B1 deals with the task of producing long-lasting hair colorations using pigments. The paper teaches that when a combination of pigment, organic silicon compound, hydrophobic polymer and a solvent is used on hair, it is possible to create colorations that are said to be particularly resistant to shampooing. For example, 3-aminopropyl-triethoxysilane was used as the organic silicon compound.

In WO 2018/115059 A1 a dyeing process is described, which runs in several steps. One step involves the application of an organosilane, and another step involves the application of a direct dye to the hair. This process is also used to achieve dyeing's with good wash fastness properties. The silanes used in this writing are for example 3-aminopropyltriethxoysilane and methyltrimethoxysilane.

In the dyeing processes of EP 2168633 B1 and WO 2018/115059 A1, organosilicon compounds from the group of silanes are used, the molecular structure of these silanes comprising at least one hydroxy group and/or hydrolysable group. Due to the presence of hydroxy groups or hydrolysable groups, silanes are reactive substances that hydrolyze or oligomerize or polymerize in the presence of water. When applied to the keratin material, the oligomerization or polymerization of the silanes initiated by the presence of water ultimately leads to the formation of a film which fixes the coloring compounds and thus produces very long-lasting colorations.

A prerequisite for a particularly long-lasting coloration on the hair is, on the one hand, good wash fastness, i.e., the film produced on the hair should not wash off because of treatments with aqueous surfactant solutions such as those used in common shampooing.

Apart from shampooing, however, hair is also subject to other stresses in the daily routine, such as the mechanical stress that occurs, for example, when combing, brushing, and styling. A coloring that is in the form of a colored film on the outside of each hair fiber is quite sensitive to the bending, traction and friction of the hair that occurs during combing.

If adhesion is poor or too brittle, the colored film may flake off the hair fiber. In this case, after combing or brushing, the user perceives a reduced color intensity, an irregularity in the coloring and, in the worst case, a mottled color result.

During the reworking of the dyeing processes disclosed in EP 2168633 B1 and WO 2018/115059 A1, it has now become apparent that the dyeing results obtained during these processes still have potential for improvement about their mechanical resistance. The dyeing's obtained in these processes were not yet sufficiently stable to repeated combing and consequently did not yet possess a sufficiently high rub fastness.

BRIEF SUMMARY

The purpose of the present disclosure was to provide a dyeing system with fastness properties comparable to those of oxidative dyeing. Wash fastness properties should be outstanding, but the use of oxidation dye precursors normally used for this purpose should be avoided. A technology was sought that would make it possible to fix the coloring compounds (such as pigments) known from the state of the art in an extremely durable way to the hair. When the agents are used in a dyeing process, intensive dyeing results with good fastness properties should be obtained. In particular, the application of the appropriate procedures should obtain particularly rub-resistant colorations, which do not suffer any weakening of color intensity even after repeated combing or styling.

Surprisingly, it has now turned out that the above-mentioned task can be excellently solved if keratinous materials, especially hair, are dyed using a procedure in which at least two agents (a) and (b) are applied to the keratinous materials (hair). Here, the agent (a) contains at least one organic silicon compound (from the group of reactive silanes) and additionally at least one silicone polymer. The agent (b) comprises at least one colorant compound selected from the group including pigments. When both agents (a) and (b) were used in a dyeing process, keratinous fibers could be dyed with high color intensity. In addition, the rub fastness of the hair dyed with (a) and (b) was excellent.

In an exemplary embodiment, a process for dyeing keratinous material is provided. The process includes applying an agent (a) to the keratinous material. The agent (a) includes at least one organic silicon compound from the group of silanes with one, two or three silicon atoms. The agent (a) further includes at least one silicone polymer. An agent (b) is applied to the keratinous material. The agent (b) includes at least one pigment.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is a method for coloring keratinous material, in particular human hair, comprising the following steps:

Application of an agent (a) to the keratinous material, wherein the agent (a) contains at least one organic silicon compound from the group of silanes with one, two or three silicon atoms, and wherein the agent (a) further contains at least one silicone polymer, and Application of an agent (b) to the keratinous material, the agent (b) comprising at least one pigment.

Keratinic Material

Keratinous material includes hair, skin, nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

Agent (a) and (b)

In the procedure as contemplated herein, agents (a) and (b) are applied to the keratinous material, in particular human hair. The two means (a) and (b) are different.

In other words, a first subject of the present disclosure is a process for dyeing keratinous material, in particular human hair, comprising the following steps:

Application of an agent (a) to the keratinous material, wherein the agent (a) contains at least one organic silicon compound from the group of silanes with one, two or three silicon atoms, and wherein the agent (a) further contains at least one silicone polymer, and Application of an agent (b) to the keratinous material, the agent (b) comprising at least one pigment, the two agents (a) and (b) being different from each other.

Agent (a)

As a first ingredient essential to the present disclosure, the composition (a) contains at least one organic silicon compound selected from silanes having one, two or three silicon atoms.

As already described, the organic silicon compounds or organic silanes contained in agent (a) are reactive compounds.

The agent (a) contains the organic silicon compound(s) from the group of silanes in a cosmetic carrier, which may be water-containing, water-poor or also water-free. In addition, the cosmetic carrier can be liquid, gel-like, creamy, powdery, or even solid (e.g., in the form of a tablet or pellet). Preferably, the cosmetic carrier of the product (a) is an aqueous or aqueous-alcoholic carrier. To hair coloration, such carriers are, for example, creams, emulsions, gels, or surfactant-containing foaming solutions, such as shampoos, foam aerosols, foam formulations or other preparations suitable for application to the hair.

The cosmetic carrier preferably contains water, which means that the carrier contains at least about 2% by weight of water based on its weight. Preferably, the water content is above about 5 wt. %, further preferably above about 10 wt. % still further preferably above about 15 wt. %. The cosmetic carrier can also be aqueous alcoholic. Aqueous/alcoholic solutions in the context of the present disclosure are aqueous solutions containing from about 2 to about 70% by weight of a C i-$C_4$ alcohol, more particularly ethanol or isopropanol. The agents as contemplated herein may additionally contain other organic solvents, such as methoxybutanol, benzyl alcohol, ethyl diglycol or 1,2-propylene glycol. Preferred are all water-soluble organic solvents.

The term "coloring agent" is used in the context of this present disclosure for a coloring of the keratin material, in particular the hair, caused using pigments. During this coloring process, the coloring compounds are deposited in a particularly homogeneous and smooth film on the surface of the keratin material. The film is formed in situ by oligomerization or polymerization of the organic silicon compound(s), as well as by the interaction of organic silicon compound with the colorant compound.

Organic Silicon Compounds

As the first ingredient essential to the present disclosure, the agent (a) contains at least one organic silicon compound selected from the group including silanes having one, two or three silicon atoms.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds of the present disclosure are compounds containing one to three silicon atoms. Organic silicon compounds preferably contain one or two silicon atoms.

According to IUPACrules, the term silane chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

The agent (a) contains at least one organic silicon compound selected from silanes having one, two or three silicon atoms. wherein the organic silicon compound preferably comprises one or more hydroxyl groups or hydrolysable groups per molecule.

In a particularly preferred embodiment, a method as contemplated herein is exemplified by the application of an agent (a) to the keratinous material, said agent (a) comprising at least one organic silicon compound selected from silanes having one, two or three silicon atoms, said organic silicon compound further comprising one or more hydroxyl groups or hydrolysable groups per molecule.

In a particularly preferred embodiment, a method as contemplated herein is exemplified by the application of an agent (a) to the keratinous material, said agent (a) comprising at least one organic silicon compound selected from silanes having one, two or three silicon atoms, said organic silicon compound further comprising one or more basic chemical functions and one or more hydroxyl groups or hydrolysable groups per molecule.

This basic group can be, for example, an amino group, an alkylamino group or a dialkylamino group, which is preferably connected to a silicon atom via a linker. The basic group is preferably an amino group, a $C_1$-$C_6$ alkylamino group or a Di($C_1$-$C_6$)alkylamino group.

The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably contains a structural unit R'R''R'''Si—O—$CH_2$—$CH_3$. The residues R', R'' and R''' represent the three remaining free valences of the silicon atom.

A particularly preferred method as contemplated herein the composition comprises (a) at least one organic silicon compound selected from silanes having one, two or three silicon atoms, the organic silicon compound preferably comprising one or more basic chemical functions and one or more hydroxyl groups or hydrolysable groups per molecule.

Particularly good results could be obtained if the agent as contemplated herein (a) contains at least one organic silicon compound of formula (I) and/or (II).

The compounds of formulae (I) and (II) are organic silicon compounds selected from silanes having one, two or three silicon atoms, the organic silicon compound comprising one or more hydroxyl groups and/or hydrolysable groups per molecule.

In another very particularly preferred embodiment, a process as contemplated herein an agent (a) is applied to the keratinous material (or human hair), the agent (a) comprising at least one organic silicon compound (a) of the formula (I) and/or (II),

        (I), where $R_1$, $R_2$ independently represent a hydrogen atom or a $C_1$-$C_6$ alkyl group, L is a linear or branched divalent $C_1$-$C_{20}$ alkylene group, R3 represents a hydrogen atom or a $C_1$-$C_6$ alkyl group R4 represents a $C_1$-$C_6$ alkyl group a, stands for an integer from 1 to 3, and b stands for the integer 3-a,

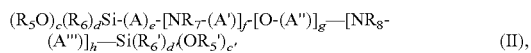        (II), where

R5, R5', R5'' independently represent a hydrogen atom or a $C_1$-$C_6$ alkyl group, R6, R6' and R6'' independently represent a $C_1$-$C_6$ alkyl group, A, A', A'', A''' and A'''' independently of one another represent a linear or branched divalent $C_1$-$C_{20}$ alkylene group $R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

        (III), c, stands for an integer from 1 to 3, d stands for the integer 3-c, c' stands for an integer from 1 to 3, d' stands for the integer 3-c', c'' stands for an integer from 1 to 3, d'' stands for the integer 3-c'', e stands for 0 or 1, f stands for 0 or 1, g stands for 0 or 1, h stands for 0 or 1, provided that at least one of e, f, g, and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A, A', A'', A''' and A'''' in the compounds of formula (I) and (II) are explained below as examples: Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—) and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In the organic silicon compounds of the formula (I)

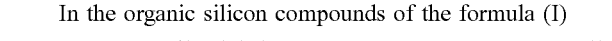        (I), the radicals $R_1$ and $R_2$ independently of one another represent a hydrogen atom or a $C_1$-$C_6$ alkyl group. In particular, the radicals $R_1$ and $R_2$ both represent a hydrogen atom.

In the middle part of the organic silicon compound is the structural unit or the linker -L- which stands for a linear or branched, divalent $C_1$-$C_{20}$ alkylene group.

Preferably -L- stands for a linear, divalent $C_1$-$C_{20}$ alkylene group. Further preferably -L- stands for a linear divalent $C_1$-$C_6$ alkylene group. Particularly preferred -L- stands for a methylene group (—$CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

The organic silicon compounds of formula (I)

        (I), one end of each carries the silicon-containing group —Si($OR_3$)$_a$($R_4$)$_b$ In the terminal structural unit —Si($OR_3$)$_a$($R_4$)$_b$, $R_3$ is hydrogen or $C_1$-$C_6$ alkyl group, and $R_4$ is $C_1$-$C_6$ alkyl group. $R_3$ and $R_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Dyes with the best wash fastness values could be obtained if the pretreatment agent contains at least one organic silicon compound corresponding to formula (I): in which $R_3$, $R_4$ independently of one another represent a methyl group or an ethyl group.

Furthermore, dyeing's with the best wash fastness properties could be obtained if the agent as contemplated herein contains at least one organic silicon compound of formula (I) in which the radical a represents the number 3. In this case the rest b stands for the number 0.

In another preferred embodiment, an agent as contemplated herein contains (a) at least one organic silicon compound of formula (I), where $R_3$, $R_4$ independently of one another represent a methyl group or an ethyl group and
a stands for the number 3 and
b stands for the number 0.

In another preferred embodiment, a process as contemplated herein the agent (a) contains at least one organic silicon compound of formula (I), $R_1R_2N\text{-}L\text{-}Si(OR_3)_a(R_4)_b$     (I), where
$R_1$, $R_2$ both represent a hydrogen atom, and
L represents a linear, divalent $C_1$-$C_6$-alkylene group, preferably a propylene group (—$CH_2$—$CH_2$—$CH_2$—) or an ethylene group (—$CH_2$—$CH_2$—),
$R_3$ represents a hydrogen atom, an ethyl group, or a methyl group,
$R_4$ represents a methyl group or an ethyl group,
a stands for the number 3 and
b stands for the number 0.

Organic silicon compounds of the formula (I) which are particularly suitable for solving the problem as contemplated herein are

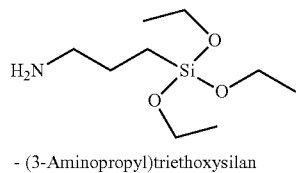
- (3-Aminopropyl)triethoxysilan

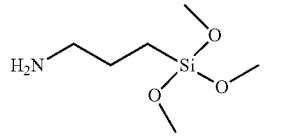
- (3-Aminopropyl)trimethoxysilane

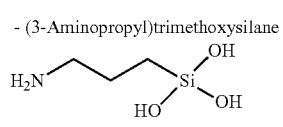
-1-(3-Aminopropyl)silantriol

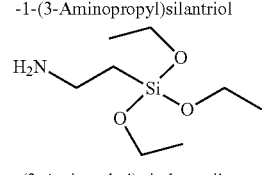
- (2-Aminoethyl)triethoxysilan

-continued

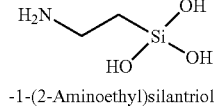
- (2-Aminoethyl)triethoxysilane

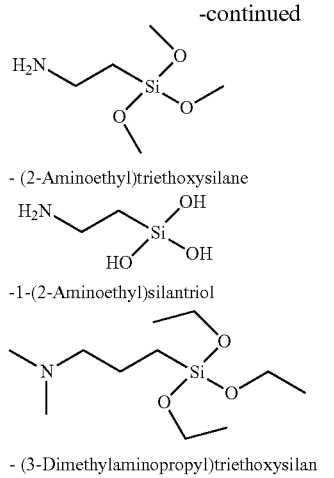
-1-(2-Aminoethyl)silantriol

- (3-Dimethylaminopropyl)triethoxysilan

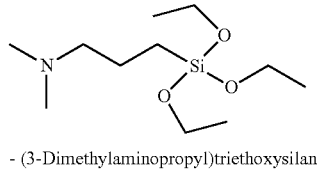
- (3-Dimethylaminopropyl)trimethoxysilane

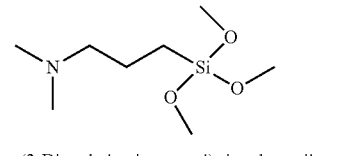
-1-(3-Dimethylaminopropyl)silantriol

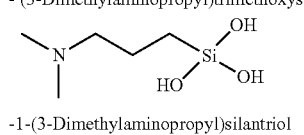
-(2-Dimethylaminoethyl)trimethoxysilan.

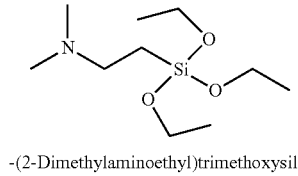
-(2-Dimethylaminoethyl)trimethoxysilane and/or

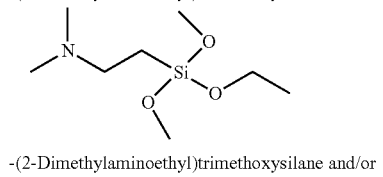
-1-(2-Dimethylaminoethyl)silantriol

In a further preferred embodiment, a process as contemplated herein the agent (a) comprises at least one organic silicon compound of formula (I) selected from the group including
(3-Aminopropyl)triethoxysilan
(3-Aminopropyl)trimethoxysilane
1-(3-Aminopropyl)silantriol
(2-Aminoethyl)triethoxysilan
(2-Aminoethyl)trimethoxysilane
1-(2-Aminoethyl)silantriol
(3-Dimethylaminopropyl)triethoxysilan
(3-Dimethylaminopropyl)trimethoxysilane
1-(3-Dimethylaminopropyl)silantriol
(2-Dimethylaminoethyl)triethoxysilan.
(2-Dimethylaminoethyl)trimethoxysilane and/or
1-(2-Dimethylaminoethyl)silantriol.

The organic silicon compound of formula (I) is commercially available. (3-aminopropyl)trimethoxysilane, for example, can be purchased from Sigma-Aldrich. Also (3-aminopropyl)triethoxysilane is commercially available from Sigma-Aldrich.

In a further version, the present disclosure contains at least one organic silicon compound of formula (II)

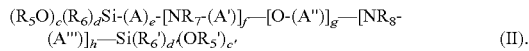
$$(R_5O)_c(R_6)_aSi-(A)_e-[NR_7-(A')]_f-[O-(A'')]_g-[NR_8-(A''')]_h-Si(R_6')_{d'}(OR_5')_{c'} \quad \text{(II)}$$

The organosilicon compounds of formula (II) as contemplated herein each carry the silicon-containing groups $(R_5O)_c(R_6)_aSi-$ and $-Si(R_6')_{d'}(OR_5')_{c'}$ at both ends.

In the central part of the molecule of formula (II) there are the groups $-(A)_e-$ and $-[NR_7-(A')]_f-$ and $[O-(A'')]_g-$ and $-[NR_8-(A''')]_h-$. Here, each of the radicals e, f, g, and h can independently of one another stand for the number 0 or 1, with the proviso that at least one of the radicals e, f, g, and h is different from 0. In other words, an organic silicon compound of formula (II) as contemplated herein contains at least one grouping from the group including -(A)- and $-[NR_7-(A')]-$ and $-[O-(A'')]-$ and $-[NR8-(A''')]-$.

In the two terminal structural units $(R_5O)_c(R_6)_aSi-$ and $-Si(R_6')_{d'}(OR_5')_{c'}$, the radicals $R_5$, $R_5'$, $R_5''$ independently of one another represent a hydrogen atom or a $C_1$-$C_6$ alkyl group. The radicals $R_6$, $R_6'$ and $R_6''$ independently represent a $C_1$-$C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing's with the best wash fastness values could be obtained if the residues c and c' both stand for the number 3. In this case d and d' both stand for the number 0.

In another preferred embodiment, a process as contemplated herein the agent (a) contains at least one organic silicon compound of formula (II),

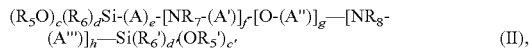
$$(R_5O)_c(R_6)_aSi-(A)_e-[NR_7-(A')]_f-[O-(A'')]_g-[NR_8-(A''')]_h-Si(R_6')_{d'}(OR_5')_{c'} \quad \text{(II),}$$

where
R5 and R5' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

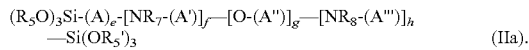
$$(R_5O)_3Si-(A)_e-[NR_7-(A')]_f-[O-(A'')]_g-[NR_8-(A''')]_h-Si(OR_5')_3 \quad \text{(IIa).}$$

The radicals e, f, g, and h can independently stand for the number 0 or 1, whereby at least one radical from e, f, g, and h is different from zero. The abbreviations e, f, g, and h thus define which of the groupings $-(A)_e-$ and $-[NR_2-(A')]f-$ and $-[O-(A'')]_g$ and $-[NR_8-(A''')]_h-$ are in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. Especially preferred e and f both stand for the number 1. Furthermore, g and h both stand for the number 0.

If e and f both stand for the number 1 and g and h both stand for the number 0, the organic silicon compound as contemplated herein corresponds to formula (IIb)

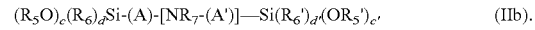
$$(R_5O)_c(R_6)_aSi-(A)-[NR_7-(A')]-Si(R_6')_{d'}(OR_5')_{c'}. \quad \text{(IIb).}$$

The radicals A, A', A'', A''' and A'''' independently represent a linear or branched divalent $C_1$-$C_{20}$ alkylene group. Preferably the radicals A, A', A'', A''' and A'''' independently of one another represent a linear, divalent $C_1$-$C_{20}$ alkylene group. Further preferably the radicals A, A', A'', A''' and A'''' independently represent a linear divalent $C_1$-$C_6$ alkylene group. In particular, the radicals A, A', A'', A''' and A'''' independently of one another represent a methylene group ($-CH_2-$), an ethylene group ($-CH_2-CH_2-$), a propylene group ($-CH_2-CH_2-CH_2-$) or a butylene group ($-CH_2-CH_2-CH_2-CH_2-$). In particular, the residues A, A', A'', A''' and A'''' stand for a propylene group ($-CH_2-CH_2-CH_2-$).

If the radical f represents the number 1, then the organic silicon compound of formula (II) as contemplated herein contains a structural grouping $-[NR_7-(A')]-$. If the radical f represents the number 1, then the organic silicon compound of formula (II) as contemplated herein contains a structural grouping $-[NR_8-(A''')]-$.

Wherein $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (III)

$$-(A'''')-Si(R_6'')_{d''}(OR_5'')_{c''} \quad \text{(III).}$$

Very preferably the radicals $R_7$ and $R_8$ independently of one another represent a hydrogen atom, a methyl group, a 2-hydroxyethyl group, a 2-alkenyl group, a 2-aminoethyl group or a grouping of the formula (III).

If the radical f represents the number 1 and the radical h represents the number 0, the organic silicon compound as contemplated herein contains the grouping [$NR_7-(A')$] but not the grouping $-[NR_8-(A''')]$ If the radical R7 now stands for a grouping of the formula (III), the pretreatment agent (a) contains an organic silicon compound with 3 reactive silane groups.

In another preferred embodiment, a process as contemplated herein the agent (a) contains at least one organic silicon compound of formula (II),

$$(R_5O)_c(R_6)_aSi-(A)_e-[NR_7-(A')]_f-[O-(A'')]_g-[NR_8-(A''')]_h-Si(R_6')_{d'}(OR_5')_{c'} \quad \text{(II),}$$

where
e and f both stand for the number 1,
g and h both stand for the number 0,
A and A' independently represent a linear, divalent $C_1$-$C_6$ alkylene group and
R7 represents a hydrogen atom, a methyl group, a 2-hydroxyethyl group, a 2-alkenyl group, a 2-aminoethyl group or a group of formula (III).

In a further preferred embodiment, a process as contemplated herein the agent (a) contains at least one organic silicon compound of the formula (II), where
e and f both stand for the number 1,
g and h both stand for the number 0,
A and A' independently of one another represent a methylene group ($-CH_2-$), an ethylene group ($-CH_2-CH_2-$) or a propylene group ($-CH_2-CH_2-CH_2$),
and
R7 represents a hydrogen atom, a methyl group, a 2-hydroxyethyl group, a 2-alkenyl group, a 2-aminoethyl group or a group of formula (III).

Organic silicon compounds of the formula (II) which are well suited for solving the problem as contemplated herein are

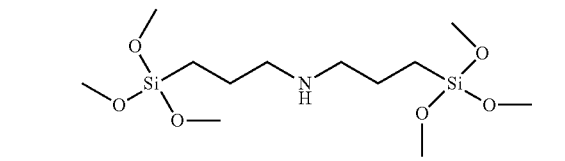
- 3-(trimethoxysilyl)-N-[3-(trimethoxysilyl)propyl]-1-propanamine

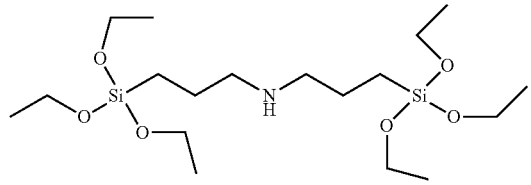
- 3-(Triethoxysilyl)-N-[3-(triethoxysilyl)propyl]-1-propanamine

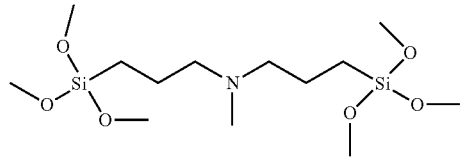
- N-methyl-3-(trimethoxysilyl)-N-[3-(trimethoxysilyl)propyl]-1-propanamine

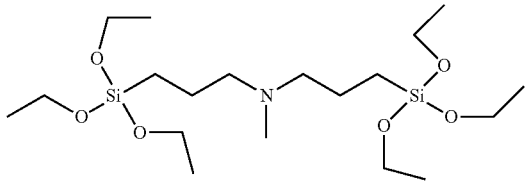
- N-methyl-3-(triethoxysilyl)-N-[3-(triethoxysilyl)propyl]-1-propanamine

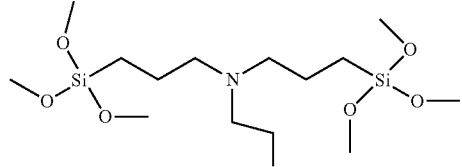
- 2-[Bis[3-(trimethoxysilyl)propyl]amino]-ethanol

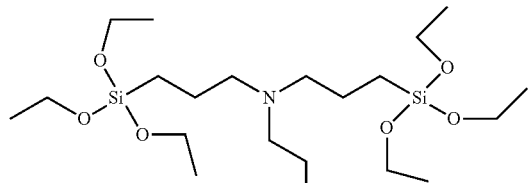
- 2-[bis[3-(triethoxysilyl)propyl]amino]-ethanol

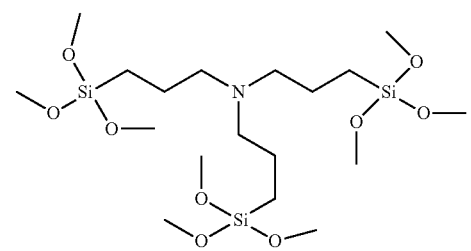
- 3-(Trimethoxysilyl)-N,N-bis[3-(trimethoxysilyl)propyl]-1-propanamine

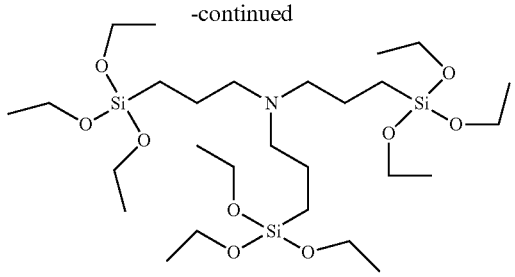
- 3-(Triethoxysilyl)-N,N-bis[3-(triethoxysilyl)propyl]-1-propanamine

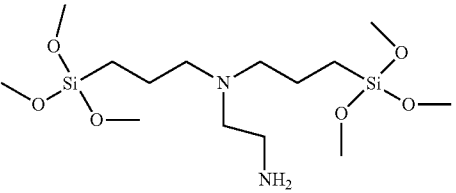
- N1,N1-Bis[3-(trimethoxysilyl)propyl]-1,2-ethanediamine,

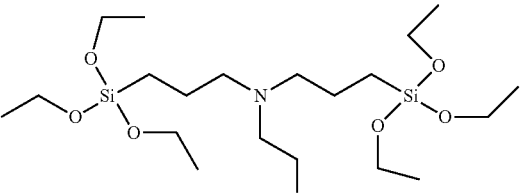
- N1,N1-Bis[3-(triethoxysilyl)propyl]-1,2-ethanediamine,

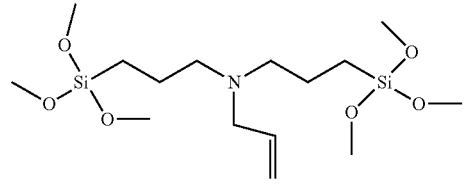
- N,N-Bis[3-(trimethoxysilyl)propyl]-2-propen-1-amine

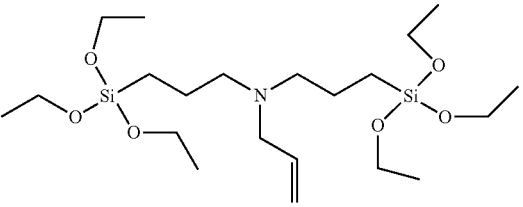
- N,N-Bis[3-(triethoxysilyl)propyl]-2-propen-1-amine

The organic silicon compounds of formula (II) are commercially available.
Bis(trimethoxysilylpropyl)amines with the CAS number 82985-35-1 can be purchased from Sigma-Aldrich.
Bis[3-(triethoxysilyl)propyl]amines with the CAS number 13497-18-2 can be purchased from Sigma-Aldrich, for example.
N-methyl-3-(trimethoxysilyl)-N-[3-(trimethoxysilyl)propyl]-1-propanamine is alternatively referred to as bis(3-trimethoxysilylpropyl)-N-methylamine and can be purchased commercially from Sigma-Aldrich or Fluorochem.
3-(triethoxysilyl)-N,N-bis[3-(triethoxysilyl)propyl]-1-propanamine with the CAS number 18784-74-2 can be purchased for example from Fluorochem or Sigma-Aldrich.
In another preferred embodiment, an agent as contemplated herein contains (a) at least one organic silicon compound of formula (II) selected from the group including 3-(trimethoxysilyl)-N-[3-(trimethoxysilyl)propyl]-1-propanamine 3-(Triethoxysilyl)-N-[3-(triethoxysilyl)propyl]-1-propanamine N-methyl-3-(trimethoxysilyl)-N-[3-(trimethoxysilyl)propyl]-1-propanamine N-Methyl-3-(triethoxysilyl)-N-[3-(triethoxysilyl)propyl]-1-propanamine 2-[Bis[3-(trimethoxysilyl)propyl]amino]-ethanol 2-[bis[3-(triethoxysilyl)propyl]amino]ethanol 3-(Trimethoxysilyl)-N,N-bis[3-(trimethoxysilyl)propyl]-1-propanamine 3-(Triethoxysilyl)-N,N-bis[3-(triethoxysilyl)propyl]-1-propanamine N1,N1-bis[3-(trimethoxysilyl)propyl]-1,2-ethanediamine, N1,N1-bis[3-(triethoxysilyl)propyl]-1,2-ethanediamine, N,N-bis[3-(trimethoxysilyl)propyl]-2-propen-1-amine and/or N,N-bis[3-(triethoxysilyl)propyl]-2-propen-1-amine In further dyeing tests, it has also proved to be particularly advantageous if the agent used on the keratinous material in the process as contemplated herein (a) contains at least one organic silicon compound of formula (IV)

$$R_9Si(OR_{10})_k(R_{11})_m \quad (IV).$$

The compounds of formula (IV) are organic silicon compounds selected from silanes having one, two or three silicon atoms, the organic silicon compound comprising one or more hydroxyl groups and/or hydrolysable groups per molecule.

The organic silicon compound(s) of formula (IV) may also be called a silane of the alkyl-alkoxy-silane or alkyl-hydroxy-silane type, $$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In another preferred embodiment, a process as contemplated herein the agent (a) contains at least one organic silicon compound of formula (IV).

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a further preferred embodiment, a process as contemplated herein the agent (a) contains, in addition to the organic silicon compound(s) of formula (I), at least one further organic silicon compound of formula (IV)

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a further preferred embodiment, a process as contemplated herein the agent (a) contains, in addition to the organic silicon compound or compounds of the formula (II), at least one further organic silicon compound of the formula (IV)

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a further preferred embodiment, a process as contemplated herein the composition contains (a) in addition to the organic silicon compound(s) of formula (I) and/or (II) at least one further organic silicon compound of formula (IV)

$$R_9Si(OR_{10})_k(R_{11})_m \quad (IV),$$

where
$R_9$ represents a $C_1$-$C_{12}$, alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In the organic silicon compounds of formula (IV), the radical $R_9$ represents a $C_1$-$C_{12}$ alkyl group. This $C_1$-$C_{12}$ alkyl group is saturated and can be linear or branched. Preferably $R_9$ stands for a linear $C_1$-$C_8$ alkyl group. Preferably $R_9$ stands for a methyl group, an ethyl group, an n-propyl group, an n-butyl group, an n-pentyl group, an n-hexyl group, an n-octyl group or an n-dodecyl group. Particularly preferred, $R_9$ stands for a methyl group, an ethyl group or an n-octyl group.

In the organic silicon compounds of formula (IV), the radical $R_{10}$ represents a hydrogen atom or a $C_1$-$C_6$ alkyl group. $R_{10}$ stands for a methyl group or an ethyl group.

In the organic silicon compounds of formula (IV), the radical Ru represents a $C_1$-$C_6$ alkyl group. $R_{11}$ stands for a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Dyes with the best wash fastness values could be obtained if an agent (a) were used in the process which contains at least one organic silicon compound of the formula (IV) in which the radical k stands for the number 3. In this case the rest m stands for the number 0.

Organic silicon compounds of the formula (IV) which are particularly suitable for solving the problem as contemplated herein are

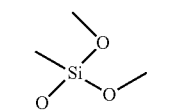

-Methyltrimethoxysilane

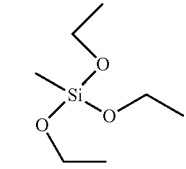

-Methyltriethoxysilane

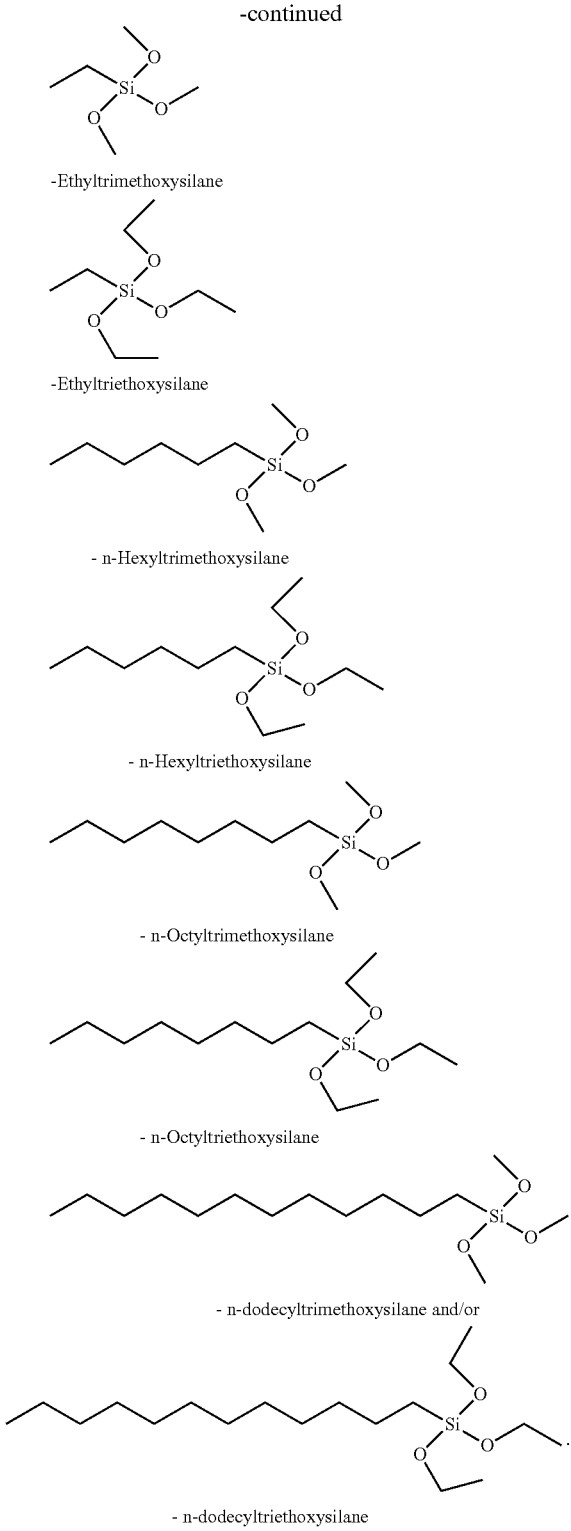

- Ethyltrimethoxysilane
- Ethyltriethoxysilane
- n-Hexyltrimethoxysilane
- n-Hexyltriethoxysilane
- n-Octyltrimethoxysilane
- n-Octyltriethoxysilane
- n-dodecyltrimethoxysilane and/or
- n-dodecyltriethoxysilane In another preferred embodiment, a process as contemplated herein the agent (a) contains at least one organic silicon compound of formula (IV) selected from the group including
Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane and/or
Dodecyltriethoxysilane.

In an explicitly particularly preferred embodiment, a process as contemplated herein an agent (a) is applied to the keratinous material which contains at least one organic silicon compound of the formula (I) which is selected from the group including (3-aminopropyl)triethoxysilane and (3-aminopropyl)trimethoxysilane, and additionally contains at least one organic silicone compound of formula (IV) selected from the group including methyltrimethoxysilane, methyltriethoxysilane, ethyltrimethoxysilane and ethyltriethoxysilane.

The organic silicon compounds described above are reactive compounds. In this context, it has been found preferable if the agent (a) as contemplated herein contains—based on the total weight of the agent (a)—one or more organic silicon compounds from the group of silanes having one, two or three silicon atoms in a total amount of from about 0.1 to about 20.0% by weight, preferably from about 1.0 to about 15.0% by weight and particularly preferably from about 2.0 to about 8.0% by weight.

In a further preferred embodiment, a process as contemplated herein the agent (a)—based on the total weight of agent (a)—contains one or more organic silicon compounds in a total amount of from about 0.1 to about 20.0% by weight, preferably from about 1.0 to about 15.0% by weight and particularly preferably from about 2.0 to about 8.0% by weight.

To achieve particularly good dyeing results, it is particularly advantageous to use the organic silicon compounds of the formula (I) and/or (II) in certain quantity ranges on average (a). Particularly preferably, the agent (a) contains—based on the total weight of the agent (a)—one or more organic silicon compounds of the formula (I) and/or (II) in a total amount of from about 0.1 to about 10.0% by weight, preferably from about 0.5 to about 5.0% by weight and particularly preferably from about 1.0 to about 3.0% by weight.

In a further preferred embodiment, a process as contemplated herein the agent (a) contains—based on the total weight of the agent (a)—one or more organic silicon compounds of the formula (I) and/or (II) in a total amount of from about 0.1 to about 10.0% by weight, preferably from about 0.5 to about 5.0% by weight and particularly preferably from about 1.0 to about 3.0% by weight.

Furthermore, it has proven to be particularly preferred if the organic silicon compound(s) of formula (IV) is (are) also present in certain quantity ranges in average (a). Particularly preferably the agent (a) contains—based on the total weight of agent (a)—one or more organic silicon compounds of the formula (IV) in a total amount of from about 0.1 to about 20.0% by weight, preferably from about 2.0 to about 15.0% by weight and particularly preferably from about 4.0 to about 9.0% by weight.

In a further preferred embodiment, a process as contemplated herein the agent (a) contains—based on the total weight of the agent (a)—one or more organic silicon compounds of the formula (IV) in a total amount of from about 0.1 to about 20.0% by weight, preferably from about 2.0 to about 15.0% by weight and particularly preferably from about 4.0 to about 9.0% by weight.

In the course of the work leading to this present disclosure it turned out that particularly stable and uniform films could be obtained on the keratin material if the agent (a) contains two structurally different organic silicon compounds.

In another preferred embodiment, a process as contemplated herein the agent (a) contains at least two structurally different organic silicon compounds.

In an explicitly particularly preferred embodiment, a process as contemplated herein an agent (a) is applied to the keratinous material which contains at least one organic silicon compound of the formula (I) which is selected from the group including (3-aminopropyl)triethoxysilane and (3-aminopropyl)trimethoxysilane, and additionally contains at least one organic silicon compound of the formula (IV) which is selected from the group including methyltrimethoxysilane, methyltriethoxysilane, ethyltrimethoxysilane and ethyltriethoxysilane.

In a further preferred embodiment, a process as contemplated herein the agent (a)—based on the total weight of agent (a)—contains:

from about 0.5 to about 3.0 weight % of at least one first organic silicon compound selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and (2-dimethylaminoethyl)triethoxysilane, and from about 3.2 to about 10.0% by weight of at least one second organic silicon compound selected from the group of methyltrimethoxysilane, methyltriethoxysilane, ethyltrimethoxysilane, ethyltriethoxysilane, octyltrimethoxysilane, octyltriethoxysilane, dodecyltrimethoxysilane and dodecyltriethoxysilane.

In this version, the agent contains (a) one or more organic silicon compounds of a first group in a total amount of from about 0.5 to about 3.0% by weight. The organic silicon compounds of this first group are selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and/or (2-dimethylaminoethyl)triethoxysilane.

In this version, the agent contains (a) one or more organic silicon compounds of a second group in a total amount of from about 3.2 to about 10.0% by weight. The organic silicon compounds of this second group are selected from the group of methyltrimethoxysilane, methyltriethoxysilane, ethyltrimethoxysilane, ethyltriethoxysilane, octyltrimethoxysilane, octyltriethoxysilane, dodecyltrimethoxysilane and/or dodecyltriethoxysilane.

Silicone Polymers

As a second ingredient essential to the present disclosure, the agent (a) contains at least one silicone polymer.

Silicone polymers, which can alternatively be called silicones for short, are understood to be poly(organo)siloxanes. Silicone polymers are a group of synthetic polymers in which silicon atoms are linked via oxygen atoms.

Silicone polymers are generally macromolecules with a molecular weight of at least about 500 g/mol, preferably at least about 1000 g/mol, more preferably at least about 2500 g/mol, particularly preferably at least about 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than about $10^7$ g/mol, preferably not more than about $10^6$ g/mol, and particularly preferably not more than about $10^5$ g/mol.

The silicone polymers comprise many Si—O repeating units, and the Si atoms may carry organic radicals such as alkyl groups or substituted alkyl groups.

Corresponding to the high molecular weight of silicone polymers, these are based on more than about 10 Si—O repeat units, preferably more than about 50 Si—O repeat units, and more preferably more than about 100 Si—O repeat units, most preferably more than about 500 Si—O repeat units.

The silicone polymers contained in agent (a) are therefore different from the silanes also contained in agent (a).

Particularly good results were obtained when an agent (a) containing an amino-functionalized silicone polymer was used in the process as contemplated herein. The amino-functionalized silicone polymer may alternatively be referred to as amino silicone.

In a further preferred embodiment, a process as contemplated herein the agent (a) comprises at least one amino-functionalized silicone polymer.

Without being committed to this theory, it is believed that the joint application of the silane and the amino silicone in means (a) results in a reaction or interaction of the two components with each other. When silane and amino silicone are used together, the silanes appear to form a film, as previously described, into which the amino silicones are either incorporated, or to which the amino silicones agglomerate. It has been found that the film formed in this way is much more supple, flexible, and less brittle. As a direct consequence, the colored films obtained after completion of the dyeing process as contemplated herein have also been shown to be much more resistant to combing and styling operations.

The agent (a) may contain one or more different amino-functionalized silicone polymers. Such silicones can be exemplified by the formula (Si-I)

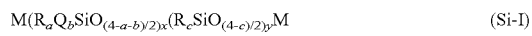

$$M(R_aQ_bSiO_{(4-a-b)/2})_x(R_cSiO_{(4-c)/2})_yM \qquad \text{(Si-I)}$$

in which formula above R is a hydrocarbon or a hydrocarbon radical having from 1 to about 6 carbon atoms, Q is a polar radical of the general formula —R'HZ wherein $R^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2.000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3$ CC(O) $OCH_2CH_2$—, —$C_6H_4C_6H_4$—, —$C_6H_4CH_2C_6H_4$—; and —$(CH_2)_3C(O)SCH_2CH_2$—.

Z is an organic amino functional residue containing at least one amino functional group. One possible formula for Z is $NH(CH_2)_zNH_2$, where z is 1 or more. Another possible formula for Z is —$NH(CH_2)_z(CH_2)_{zz}NH$, wherein both z and zz are independently 1 or more, this structure comprising diamino ring structures, such as piperazinyl. Z is most preferably an —$NHCH_2CH_2NH_2$ residue. Another possible formula for Z is —$N(CH_2)_z(CH_2)_{zz}NX_2$ or —$NX_2$, wherein each X of $X_2$ is independently selected from the group including hydrogen and alkyl groups having 1 to 12 carbon atoms, and zz is 0.

Q is most preferably a polar, amine-functional radical of the formula —$CH_2CH_2CH_2NHCH_2CH_2NH_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of $R_aQ_b$ $SiO_{(4-a-b)/2}$ units to $R_cSiO_{(4-c)/2}$ units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the agent (a) contains an amino-functional silicone polymer of formula (Si-II)

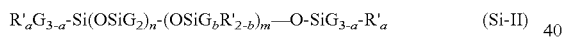  (Si-II)

wherein means:
G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—CH$(CH_3)CH_2CH_3$, $CH(CH_3)CH_2CH_3$, —O—$C(CH_3)_3$, —$C(CH_3)_3$.
a stands for a number between 0 and 3, especially 0.
b stands for a number between 0 and 1, especially 1,
m and n are numbers whose sum (m+n) is between about 1 and about 2000, preferably between about 50 and about 150, where n preferably assumes values from 0 to about 1999 and from about 49 to about 149 and m preferably assumes values from about 1 to about 2000, from about 1 to about 10,
R' is a monovalent radical selected from
—Q-N(R")—$CH_2$—$CH_2$—N(R")$_2$
—Q-N(R")$_2$
—Q-$N^+(R")_3A^-$
—Q-$N^+H(R")_2$ $A^-$
—Q-$N^+H(R")A^-$
—Q-N(R")—$CH_2$—$CH_2$—$N^+R"H_2A^-$
where each Q is a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, —$CH(CH_3)CH_2CH_2$—, R" represents identical or different radicals selected from the group including —H, -phenyl, —benzyk-$CH_2$—$CH(CH_3)$Ph, the $C_{1-20}$ alkyl radicals, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$, and A represents an anion preferably selected from chloride, bromide, iodide or methosulfate.

In the context of a further preferred embodiment, a process as contemplated herein is exemplified by the application of an agent (a) to the keratinous material, wherein the agent (a) comprises at least one amino-functional silicone polymer of formula (Si-IIa),

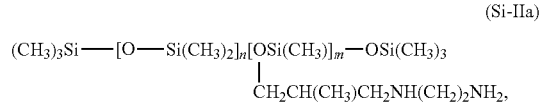  (Si-IIa)

wherein m and n are numbers whose sum (m+n) is between about 1 and about 2000, preferably between about 50 and about 150, n preferably assuming values from 0 to about 1999 and from about 49 to about 149, and m preferably assuming values from about 1 to about 2000, from about 1 to about 10.

According to the INCI declaration, these silicones are called trimethylsilylamodimethicones.

In another preferred embodiment, a method as contemplated herein is exemplified by the application of an agent (a) to the keratinous material, said agent (a) comprising at least one amino-functional silicone polymer of formula (Si-IIb)

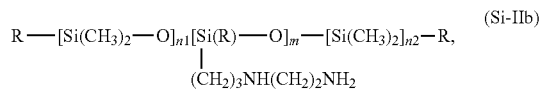  (Si-IIb)

in which R represents —OH, —O—$CH_3$ or a —$CH_3$ group and m, n1 and n2 are numbers whose sum (m+n1+n2) is between about 1 and about 2000, preferably between about 50 and about 150, the sum (n1+n2) preferably assuming values from 0 to about 1999 and from about 49 to about 149 and m preferably assuming values from about 1 to about 2000, from about 1 to about 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above about 0.25 meq/g, preferably above about 0.3 meq/g and above about 0.4 meq/g. The amine number represents the milliequivalents of amine per gram of the amino-functional silicone. The amine number represents the milliequivalents of amine per gram of the amino-functional silicone.

In the context of a further preferred embodiment, a process as contemplated herein is exemplified by the application of an agent (a) to the keratinous material, wherein the agent (a) comprises at least one amino-functional silicone polymer of the formula of formula (Si-III),

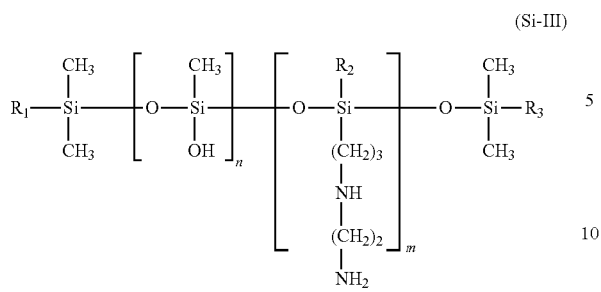
(Si-III)

where
- m and n mean numbers chosen so that the sum (n+m) is in the range from about 1 to about 1000,
- n is a number in the range 0 to about 999 and m is a number in the range from about 1 to about 1000,
- R1, R2 and R3, which are the same or different, denote a hydroxy group or a C1-4 alkoxy group,
- wherein at least one of R1 to R3 represents a hydroxy group.

Other preferred methods as contemplated herein are exemplified by the application of an agent (a) to the keratinous material, said agent (a) comprising at least amino-functional silicone polymer of formula (Si-IV)

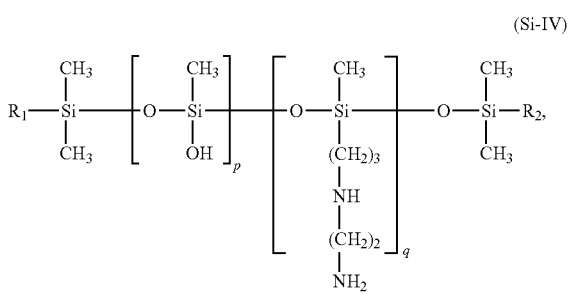
(Si-IV)

in which
- p and q mean numbers chosen so that the sum (p+q) is in the range from about 1 to about 1000,
- p is a number in the range 0 to about 999 and q is a number in the range from about 1 to about 1000,
- R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si-III) and (Si-IV), not every R1-Si(CH₃)₂ group is necessarily bonded to an —[O—Si(CH₃)₂] grouping.

Processes as contemplated herein in which an agent (a) containing at least one amino-functional silicone polymer of the formula (Si-V) is applied to the keratin fibers have also proven to be particularly effective with respect to the desired effects

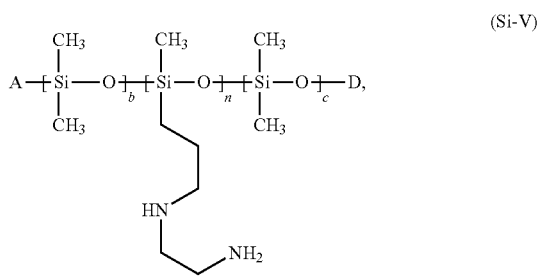
(Si-V)

located in the
- A represents a group —OH, —O—Si(CH₃)₃, —O—Si(CH₃)₂OH, —O—Si(CH₃)₂OCH₃,
- D represents a group —H, —Si(CH₃)₃, —Si(CH₃)₂OH, —Si(CH₃)₂OCH₃,
- b, n, and c stand for integers between 0 and 1000,
- with the specifications
  - n>0 and b+c>0
  - at least one of the conditions A=—OH or D=—H is fulfilled.

In the above formula (Si-V), the individual siloxane units are statistically distributed with the indices b, c, and n, i.e., they do not necessarily have to be block copolymers.

The best effects in terms of improving rub fastness were observed when an agent (a) containing a special 4-morpholinomethyl-substituted silicone polymer was applied to the keratin material in the processes as contemplated herein. This very particularly preferred amino-functionalized silicone polymer comprises structural units of the formulae (SI-VI) and of the formula (Si-VII)

(Si-VI)

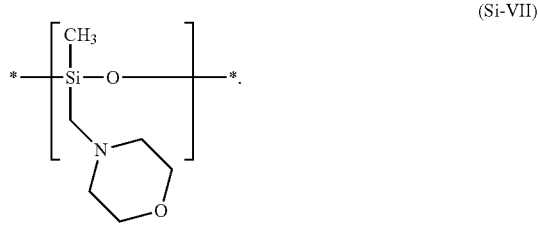
(Si-VII)

In an explicitly quite particularly preferred embodiment, a process as contemplated herein the agent (a) contains at least one amino-functionalized silicone polymer comprising structural units of the formula (SI-VI) and of the formula (Si-VII)

(Si-VI)

(Si-VII)

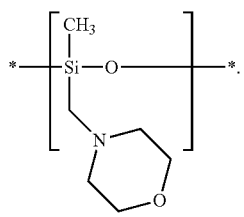

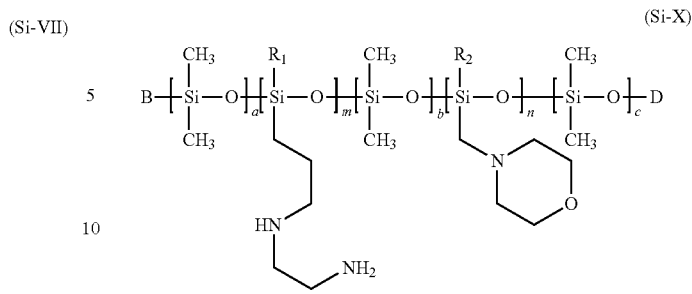

(Si-X)

Corresponding 4-morpholinomethyl-substituted silicone polymers are described below.

A very particularly preferred amino-functionalized silicone polymer is known by the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VI), (Si-VIII) and (Si-IX)

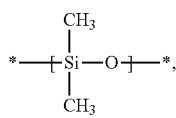

(Si-VI)

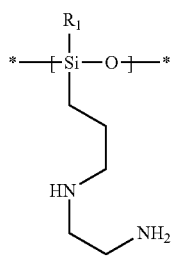

(Si-VIII)

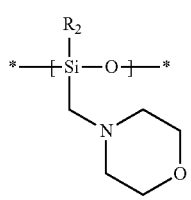

(Si-IX)

in which
R1 is —$CH_3$, —OH, —$OCH_3$, —O—$CH_2CH_3$, —O—$CH_2CH_2CH_3$, or —O—$CH(CH_3)_2$.
R2 is —$CH_3$, —OH, or —$OCH_3$.

Particularly preferred compositions (a) as contemplated herein contain at least one 4-morpholinomethyl-substituted silicone of the formula (Si-X)

located in the
R1 is —$CH_3$, —OH, —$OCH_3$, —O—$CH_2CH_3$, —O—$CH_2CH_2CH_3$, or —O—$CH(CH_3)_2$.
R2 is —$CH_3$, —OH, or —$OCH_3$. B represents a group —OH, —O—$Si(CH_3)_3$, —O—$Si(CH_3)_2OH$, —O—Si$(CH_3)_2OCH_3$,
D represents a group —H, —$Si(CH_3)_3$, —$Si(CH_3)_2OH$, —$Si(CH_3)_2OCH_3$,
a, b, and c stand independently for integers between 0 and about 1000, with the condition a+b+c>0
m and n independently of each other stand for integers between about 1 and about 1000
with the proviso that
at least one of the conditions B=—OH or D=—H is fulfilled,
the units a, b, c, m, and n are distributed statistically or block wise in the molecule.

Structural formula (Si-VI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m, and n are preferably statistically distributed.

The silicones used as contemplated herein represented by formula (Si-VI) can be trimethylsilyl-terminated (D or B=—Si(CH3)3), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—$Si(CH_3)_2OH$ and D=—$Si(CH_3)_3$
B=—O—$Si(CH_3)_2OH$ and D=—$Si(CH_3)_2OH$
B=—O—$Si(CH_3)_2OH$ and D=—$Si(CH_3)_2OCH_3$
B=—O—$Si(CH_3)_3$ and D=—$Si(CH_3)_2OH$
B=—O—$Si(CH_3)_2OCH_3$ and D=—$Si(CH_3)_2OH$
to everyone. These silicones lead to exorbitant improvements in the hair properties of the hair treated with the agents of the present disclosure, and to a seriously improved protection in oxidative treatment.

To produce particularly resistant films, the agent (a) contains the silicone polymer or polymers, in particular the amino-functionalized silicone polymers, preferably in certain ranges of amounts.

Particularly flexible films were obtained when an agent (a) was used in the process as contemplated herein which contains—based on the total weight of the agent (a)—one or more silicone polymers in a total amount of from about 0.1 to about 8.0% by weight, preferably from about 0.1 to about 5.0% by weight, more preferably from about 0.1 to about 3.0% by weight and very particularly preferably from about 0.1 to about 0.5% by weight.

In the context of a further preferred embodiment, a process as contemplated herein the agent (a) contains—based on the total weight of the agent (a)—one or more silicone polymers in a total amount of from about 0.1 to about 8.0% by weight, preferably from about 0.1 to about 5.0% by weight, more preferably from about 0.1 to about 3.0% by weight and very particularly preferably from about 0.1 to about 0.5% by weight.

In an explicitly quite particularly preferred embodiment, a process as contemplated herein the agent (a) contains—based on the total weight of the agent (a)—one or more amino-functionalized silicone polymers in a total amount of from about 0.1 to about 8.0% by weight, preferably from about 0.1 to about 5.0% by weight, more preferably from about 0.1 to about 3.0% by weight and very particularly preferably from about 0.1 to about 0.5% by weight.

Agent (b)

The agent (b) is exemplified by its content of at least one pigment. The agent (b) may also be called colorant (b).

Pigments within the meaning of the present disclosure are coloring compounds which have a solubility in water at about 25° C. of less than about 0.5 g/L, preferably less than about 0.1 g/L, even more preferably less than about 0.05 g/L. Water solubility can be determined, for example, by the method described below: about 0.5 g of the pigment are weighed in a beaker. A stir-fish is added. Then one liter of distilled water is added. This mixture is heated to about 25° C. for one hour while stirring on a magnetic stirrer. If undissolved components of the pigment are still visible in the mixture after this period, the solubility of the pigment is below about 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below about 0.5 g/L.

Suitable color pigments can be of inorganic and/or organic origin.

In a preferred embodiment, an agent (b) of the present disclosure contains at least one colorant compound from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein the agent (b) contains at least one colorant compound from the group of pigments selected from the group of colored metal oxides, metal hydroxides, metal oxide hydrates, silicates, metal sulfides, complex metal cyanides, metal sulfates, bronze pigments and/or from colored pigments based on mica or mica which are coated with at least one metal oxide and/or one metal oxychloride.

In a further preferred embodiment, an agent as contemplated herein contains (b) at least one colorant compound from the group of pigments selected from pigments based on mica or micaceous iron oxide, which is combined with one or more metal oxides from the group of titanium dioxide (CI 77891), are coated with black iron oxide (CI 77499), yellow iron oxide (CI 77492), red and/or brown iron oxide (CI 77491, CI 77499), manganese violet (CI 77742), ultramarine (sodium aluminum sulfo silicates, CI 77007, pigment blue 29), chromium oxide hydrate (CI 77289), chromium oxide (CI 77288) and/or iron blue (ferric ferrocyanides, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:

Colorona Copper, Merck, MICA, CI 77491 (IRON OXIDES)

Colorona Passion Orange, Merck, Mica, CI 77491 (Iron Oxides), Alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)
Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, the means as contemplated herein may also contain (b) one or more coloring compounds from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, a process as contemplated herein the agent (b) contains at least one colorant compound from the group of organic pigments selected from the group of carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the pigments in agent (b) of the process as contemplated herein is particularly preferred. It is also preferred if the pigments used have a certain particle size. As contemplated herein, it is therefore advantageous if the at least one pigment has an average particle size D50 of from about 1.0 to about 50 µm, preferably from about 5.0 to about 45 µm, preferably from about 10 to about 40 µm, from about 14 to about 30 µm. The mean particle size $D50D_{50}$, for example, can be determined using dynamic light scattering (DLS).

The pigment or pigments may be used in an amount of from about 0.001 to about 20% by weight, of from about 0.05 to about 5% by weight, each based on the total weight of agent (b).

Film Forming, Hydrophobic Polymer

To achieve uniform and particularly washfast dyeing's, it has further proved to be particularly preferred if the agent (b) used in the process as contemplated herein additionally contains at least one film-forming, hydrophobic polymer.

In a further preferred embodiment, a process as contemplated herein agent (b) contains at least one film-forming, hydrophobic polymer.

Polymers are macromolecules with a molecular weight of at least about 1000 g/mol, preferably of at least about 2500 g/mol, particularly preferably of at least about 5000 g/mol, which include identical, repeating organic units. The polymers of the present disclosure may be synthetically produced polymers which are manufactured by polymerisation of one type of monomer or by polymerisation of different types of monomer which are structurally different from each other. If the polymer is produced by polymerising a type of monomer, it is called a homo-polymer. If structurally different monomer types are used in polymerisation, the resulting polymer is called a copolymer.

The maximum molecular weight of the polymer depends on the degree of polymerisation (number of polymerised monomers) and the batch size and is determined by the polymerisation method. For the purposes of the present disclosure, it is preferred that the maximum molecular weight of the film-forming hydrophobic polymer (c) is not more than about 107 g/mol, preferably not more than about 106 g/mol and particularly preferably not more than about 105 g/mol.

A hydrophobic polymer is a polymer that has a solubility in water at about 25° C. (760 mmHg) of less than about 1% by weight.

The water solubility of the film-forming, hydrophobic polymer can be determined in the following way, for example. about 1.0 g of the polymer is placed in a beaker. Make up to about 100 g with water. A stir-fish is added, and the mixture is heated to about 25° C. on a magnetic stirrer while stirring. It is stirred for about 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than about 1% by weight.

As contemplated herein, a film-forming polymer is a polymer which can form a film on a substrate, for example on a keratinic material or a keratinic fiber. The formation of a film can be demonstrated, for example, by looking at the keratin material treated with the polymer under a microscope.

These include acrylic acid-type polymers, polyurethanes, polyesters, polyamides, polyureas, cellulose polymers, nitrocellulose polymers, silicone polymers, acrylamide-type polymers, and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, a process as contemplated herein the agent (b) contains at least one film-forming hydrophobic polymer selected from the group of copolymers of acrylic acid, copolymers of methacrylic acid, homopolymers or copolymers of acrylic acid esters, homopolymers or copolymers of methacrylic acid esters, the homopolymers or copolymers of acrylic acid amides, the homopolymers or copolymers of methacrylic acid amides, the copolymers of vinylpyrrolidone, the copolymers of vinyl alcohol, the copolymers of vinyl acetate, the homopolymers or copolymers of ethylene, the homopolymers or copolymers of propylene, the homopolymers or copolymers of styrene, polyurethanes, polyesters and/or polyamides The film-forming hydrophobic polymers, which are selected from the group of synthetic polymers, polymers obtainable by radical polymerisation or natural polymers, have proved to be particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinylamides, the esters or amides of (meth)acrylic acid with at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth) acrylate; isonononyl (meth)acrylate; 2-ethylhexyl (meth) acrylate; lauryl (meth)acrylate; isopentyl (meth)acrylate; n-butyl (meth)acrylate); isobutyl (meth)acrylate; ethyl (meth)acrylate; methyl (meth)acrylate; tert-butyl (meth) acrylate; stearyl (meth)acrylate; hydroxyethyl (meth)acrylate; 2-hydroxypropyl (meth)acrylate; 3-hydroxypropyl (meth)acrylate and/or mixtures thereof.

Other film-forming hydrophobic polymers may be selected from the homo- or copolymers of (meth)acrylamide; N-alkyl-(meth)acrylamides, in those with $C_2$-$C_{18}$ alkyl groups, such as N-ethyl-acrylamide, N-tert-butyl-acrylamide, le N-octyl-crylamide; N-di($C_1$-$C_4$)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Me-thacrylate Copolymer), Aculyn® 28 (Acrylates/Beheneth-25 Methacrylate Copolymer), Structure 20010 (Acryla-tes/Steareth-20 Itaconate Copolymer), Structure 30010 (Acrylates/Ceteth-20 Itaconate Copolymer), Structure Plus® (Acrylates/Aminoacrylates $C_{10}$-30 Alkyl PEG-20 Itaconate Copolymer), Carbopol® 1342, 1382, Ultrez 20, Ultrez 21 (Acrylates/$C_{10}$-30 Alkyl Acrylate Crosspolymer), Synthalen W 2000® (Acrylates/Palmeth-25 Acrylate Copolymer) or the Rohme and Haas distributed Soltex OPT (Acrylates/$C_{12}$-22 Alkyl methacrylate Copolymer).

The homo- and copolymers of N-vinylpyrrolidone, vinyl-caprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another version, block copoylmers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

Surprisingly, it turned out that particularly good dyeing's can be obtained with the anionic direct dyes, if the film-forming hydrophobic polymer also carries anionic charges.

In a further explicitly particularly preferred embodiment, a process as contemplated herein the agent (b) contains at least one anionic, film-forming, hydrophobic polymer.

An anionic polymer is a polymer comprising repeating units having at least one carboxylic acid group, one sulphonic acid group and/or their physiologically acceptable salts. In other words, an anionic polymer is made from monomers having at least one carboxylic acid group, a sulphonic acid group. In this context, the hydrophobic, film-forming copolymers of acrylic acid and the copolymers of methacrylic acid are particularly preferred. The polymers in this group contain the carboxylic acid groups, the sulphonic acid groups or their salts in an amount that ensures that the hydrophobic character of the whole polymer is maintained.

The film-forming hydrophobic polymer(s) as contemplated herein are preferably used in certain quantity ranges on average (b). In this context, it has proved to be particularly preferred for the solution of the task as contemplated herein if the agent (b)—based on the total weight of agent (b)—contains one or more polymers in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

In a further preferred embodiment, a process as contemplated herein the agent (b) contains—based on the total weight of agent (b)—one or more film-forming hydrophobic polymers in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

Other Ingredients in Products (a) and (b)

The agents (a) and (b) described above may also contain one or more optional ingredients.

The products may also contain one or more surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO$^{(-)}$— or —SO$_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkyl-betaines, alkylamidobetaines, amino propionates, aminoglycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

The products may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide. The non-ionic surfactants are used in a total quantity of from about 0.1 to about 45% by weight, preferably from about 1 to about 30% by weight and very preferably from about 1 to about 15% by weight—based on the total weight of the respective agent.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of from about 0.1 to about 45 wt. %, preferably from about 1 to about 30 wt. % and most preferably from about 1 to about 15 wt. %—based on the total weight of the respective agent.

Furthermore, the means as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of from about 0.1 to about 45 wt. %, preferably from about 1 to about 30 wt. % and most preferably from about 1 to about 15 wt. %—based on the total weight of the respective agent.

To adjust the desired pH, agents (a), (b) and (c) may also contain at least one alkalizing agent and/or acidifying agent. The pH values for the purposes of the present disclosure are pH values measured at a temperature of about 22° C.

As alkalizing agents, agents (a), (b) and (c) may contain for example ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment the agent as contemplated herein contains an alkanolamine selected from 2-aminoethan-1-ol and/or 2-amino-2-methylpropan-1-ol as alkalizing agent.

A particularly preferred embodiment the agent as contemplated herein contains an alkanolamine selected from 2-aminoethan-1-ol and/or 2-amino-2-methylpropan-1-ol as alkalizing agent. Preferred amino acids are aminocarboxylic acids, especially α-(alpha)-aminocarboxylic acids and w-aminocarboxylic acids, whereby α-aminocarboxylic acids are particularly preferred.

As contemplated herein, basic amino acids are those amino acids which have an isoelectric point pI of greater than about 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Acidifiers commonly used by experts are, for example, indulgence acids such as citric acid, acetic acid, malic acid, or tartaric acid, as well as diluted mineral acids such as hydrochloric acid, sulfuric acid, or phosphoric acid.

They may also contain other active substances, auxiliaries and additives, such as solvents, fatty components such as C8-C30 fatty alcohols, C5-C30 fatty acid triglycerides, $C_8$-$C_{30}$ fatty acid monoglycerides, $C_8$-$C_{30}$ fatty acid diglycerides and/or hydrocarbons; polymers, structural agents such as glucose, maleic acid and lactic acid; hair conditioning compounds such as phospholipids, for example lecithin and cephalins; perfume oils, dimethylisosorbide and cyclodextrins; fiber structure-improving active substances, in particular mono-, di- and oligosaccharides such as glucose, galactose, fructose, fructose and lactose; dyes for coloring the composition; anti-dandruff active substances such as Piroctone Olamine, Zinc Omadine and Climbazol; amino acids and oligopeptides; protein hydrolysates on animal and/or vegetable basis, as well as in the form of their fatty acid condensation products or optionally anionic or cationically modified derivatives; vegetable oils; sunscreens and UV-blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycumarine, hydroxybenzoic acids, catechine, tannine, leukoanthocyanidine, anthocyanidine, flavanone, flavone and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; and blowing agents such as propane-butane mixtures, $N_2O$, dimethyl ether, $CO_2$ and air.

The selection of these other substances will be made by the specialist according to the desired properties of the agents. About other optional components and the quantities of these components used, explicit reference is made to the relevant manuals known to the specialist. The additional active ingredients and auxiliary substances are preferably used in the preparations as contemplated herein in quantities of from about 0.0001 to about 25 wt. % each, from about 0.0005 to about 15 wt. %, based on the total weight of the respective agent.

Process for Dyeing Keratin Materials

In the procedure as contemplated herein, agents (a) and (b) are applied to the keratinous materials, to human hair. Thus, agents (a) and (b) are the ready-to-use agents. The agents (a) and (b) are different.

In principle, agents (a) and (b) can be applied simultaneously or successively, whereby successive application is preferred.

The best results were obtained when agent (a) was applied to the keratin materials as a pretreatment agent and then agent (b) was applied as a colorant.

Therefore, a method for dyeing keratinous material, in particular human hair, comprising the following steps in the order given is particularly preferred:

in a first step, applying an agent (a) to the keratinous material, wherein the agent (a) comprises at least one organic silicon compound selected from silanes having one, two or three silicon atoms, and wherein the agent (a) further comprises at least one silicone polymer, and in a second step, applying an agent (b) to the keratinous material, the agent (b) comprising at least one pigment.

The agents (a) and (b) are particularly preferably applied within one and the same dyeing process, which means that there is a period of a maximum of several hours between the application of agents (a) and (b).

In a further preferred embodiment, a method as contemplated herein first the agent (a) is applied, and then the agent (b) is applied, the time between the application of the agents (a) and (b) being at most about 24 hours, preferably at most about 12 hours and particularly preferably at most about 6 hours.

Within the scope of the procedure as contemplated herein, the keratin materials, in particular human hair, are first treated with agent (a). Then the actual colorant (b)—which contains the coloring compounds—is applied to the keratin materials.

Preferably, agent (a) itself does not contain colorants or coloring compounds. A characteristic feature of the pretreatment agent (a) is its content of at least one reactive organic silicon compound and at least one silicone polymer. The reactive organic silicon compound(s) (a), together with the silicone polymer, functionalize the hair surface as soon as they meet it. In this way a first, still uncolored film is formed. Here, the flexibility and resistance of the resulting film can be optimized by adding the silicone polymer. In the second step of the process, a colorant (b) is now applied to the hair. During application of the colorant (b), the colorant compounds interact with the silane film and are thus bound to the keratin materials. Here, the technical application properties of the resulting dyeing can be further improved by selecting the optimum process conditions.

In the context of a further form of execution, a procedure comprising the following steps in the order indicated is particularly preferred (1) Application of agent (a) on the keratinous material, (2) Allow the agent (a) to act for a period of from about 10 seconds to about 10 minutes, preferably from about 10 seconds to about 5 minutes, (3) if necessary, rinse the keratinous material with water, (4) Application of agent (b) on the keratinous material, (5) Allow the agent (b) to act for a period of from about 30 seconds to about 30 minutes, preferably from about 30 seconds to about 10 minutes, and (6) Rinse the keratinous material with water.

The rinsing of the keratinous material with water in steps (3) and (6) of the process is understood, as contemplated herein, to mean that only water is used for the rinsing process, without any other agents other than agents (a) and (b).

In a first step (1), agent (a) is applied to the keratin materials, especially human hair.

After application, the agent (a) can act on the keratin materials. In this context, application times from about 10 seconds to about 10 minutes, preferably from about 20 seconds to about 5 minutes and especially preferably from about 30 seconds to about 2 minutes on the hair have proven to be particularly beneficial.

In a preferred embodiment of the method as contemplated herein, the agent (a) can now be rinsed from the keratin materials before the agent (b) is applied to the hair in the subsequent step.

Dyeing's with also good wash fastness were obtained when agent (b) was applied to the keratin materials which were still exposed to agent (a).

In step (4), agent (b) is now applied to the keratin materials. After application, let the agent (b) act on the hair.

The process as contemplated herein allows the production of dyeing's with particularly good intensity and wash fastness even with a short exposure time of agent (b). Application times from about 10 seconds to about 10 minutes, preferably from about 20 seconds to about 5 minutes and most preferably from about 30 seconds to about 3 minutes on the hair have proven to be particularly beneficial.

In step (6), agent (b) (and any remaining agent (a)) is rinsed out of the keratin material with water.

In the context of a further form of execution, a procedure comprising the following steps in the order indicated is particularly preferred (1) Application of agent (a) on the keratinous material, (2) Allow the agent (a) to act for a period of from about 10 seconds to about 10 minutes, preferably from about 10 seconds to about 5 minutes, (3) if necessary, rinse the keratinous material with water, (4) Application of agent (b) on the keratinous material, (5) Allow the agent (b) to act for a period of from about 30 seconds to about 30 minutes, preferably from about 30 seconds to about 10 minutes, and (6) Rinse the keratinous material with water.

In this embodiment, the sequence of steps (1) to (6) preferably takes place within about 24 hours.

Multi-Component Packaging Unit (Kit-of-Parts)

Within the scope of the procedure as contemplated herein, agents (a) and (b) are applied to the keratin materials, i.e., both agents (a) and (b) are ready-to-use agents.

To increase user comfort, the user is preferably provided with all required resources in the form of a multi-component packaging unit (kit-of-parts).

A second subject matter of the present disclosure is therefore a multi-component packaging unit (kit-of-parts) for coloring keratinic material, comprehensively packaged separately from one another a first container comprising an agent (a), wherein the agent (a) comprises at least one organic silicon compound selected from the group including silanes having one, two or three silicon atoms, and wherein the agent (a) further comprises at least one silicone polymer, and a second container comprising an agent (b), wherein the agent (b) comprises at least one pigment.

The organic silicon compounds from the group of silanes with one, two or three silicon atoms contained in agent (a) of the kit correspond to the organic silicon compounds that were also used in agent (a) of the previously described process.

The silicone polymers contained in agent (a) of the kit correspond to the silicone polymers that were also used in agent (a) of the previously described process.

The pigments contained in agent (b) of the kit correspond to the pigments that were also used in agent (b) of the procedure described above.

A second subject matter of the present disclosure is therefore a multi-component packaging unit (kit-of-parts) for coloring keratinic material, comprehensively packaged separately from one another a first container comprising an agent (a), wherein the agent (a) comprises at least one organic silicon compound selected from the group including silanes having one, two or three silicon atoms, and wherein the agent (a) further comprises at least one silicone polymer, wherein the organic silicon compound and the silicone polymer have been disclosed in detail in the description of the first subject matter of the present disclosure, and a second container comprising an agent (b), the agent (b) comprising at least one pigment as disclosed in detail in the description of the first subject present disclosure.

The agent (a) contains with the organic silicon compound(s) a class of highly reactive compounds which can undergo hydrolysis or oligomerization and/or polymerization in the presence of water as described above. Due to their high reactivity, these organic silicon compounds form a film on the keratin material.

To avoid premature oligomerization or polymerization, it is of considerable advantage to the user to prepare the ready-to-use agent (a) only shortly before application.

In the context of a further embodiment, a multi-component packaging unit (kit-of-parts) for coloring keratinic material is preferably packaged separately from one another
- a first container comprising an agent (a1), wherein the agent (a1) comprises at least one organic silicon compound selected from the group including silanes having one, two or three silicon atoms, and wherein the agent (a1) further comprises at least one silicone polymer,
- a second container comprising an agent (a2), the agent (2) comprising water, and
- a third container containing an agent (b), the agent (b) containing at least one pigment.

To provide a formulation that is as stable as possible during storage, the agent (a1) itself is preferably packaged with low or no water.

A kit-of-parts packaging unit as contemplated herein the agent (a1)—based on the total weight of the agent (a1)—contains a water content of from about 0.001 to about 10.0% by weight, preferably from about 0.5 to about 9.0% by weight, more preferably from about 1.0 to about 8.0% by weight and very particularly preferably from about 1.5 to about 7.0% by weight.

The agent (a2) contains water. In a preferred embodiment, a multi-component packaging unit (kit-of-parts) as contemplated herein the agent (a2)—based on the total weight of the agent (a2)—has a water content of from about 15 to about 100% by weight, preferably from about 35 to about 100% by weight, more preferably from about 55 to about 100% by weight, still more preferably from about 65 to about 100% by weight and very particularly preferably from about 75 to about 100% by weight.

Within this version, the ready-to-use agent (a) is now produced by mixing agents (a1) and (a2).

For example, the user can first mix or shake the agent (a1) containing the organic silicon compound(s) with the water-containing agent (a2). The user can now apply this mixture of (a1) and (a2) to the keratin materials—either directly after their production or after a short reaction time of 10 seconds to 20 minutes. Afterwards, the user can apply agent (b) as described above.

With respect to the other preferred embodiments of the multi-component packaging unit as contemplated herein, the same applies mutatis mutandis to the procedure as contemplated herein.

EXAMPLES

1. Formulations

The following formulations were produced:

Pretreatment Agent (a)

| Agent (a1) | (a1V) Comparison | (a1E) Present disclosure |
|---|---|---|
| (3-Aminopropyl)triethoxysilan | 13.3 g | 13.3 g |
| Methyltrimethoxysilane | 66.7 g | 66.7 g |
| Amodimethicone/Morpholinomethyl Silsesquioxane Copolymer | — | 10.0 g |
| Water | 20.0 g | 10.0 g |

| Agent (a2) | (a2) |
|---|---|
| Ammonia/citric acid | ad pH 9.5 |
| Water | 100 g |

Colorant (b)

| | (b) |
|---|---|
| Xirona Caribbean Blue, Merck, Mica, CI 77891 (Titanium Dioxide), Silica, Tin Oxide | 2.0 g |
| PVP K 30 (Ashland, ISP, Polyvinylpyrrolidone) | 4.5 g |
| Dermacryl 79 (Akzo Nobel, Acrylates/Octylacrylamide Copolymer, CAS-Nr. 129702-02-9) | 4.5 g |
| Ammonia (25% aqueous solution) | ad pH 10 |
| Water | ad 100 g |

2. Application

To prepare the ready-to-use pretreatment agent (a), the indicated amount of agent (a1V) and (a1E) were mixed with the indicated amount of agent (a2) with shaking. Afterwards the agent (a) was left to stand for 15 minutes. The agent (a) is the ready-to-use agent. One strand of hair (Kerling, Euronatural hair white) was dipped into the medium (a) and left in it for 1 minute. Afterwards, excess product (a) was stripped from each strand of hair. Each strand of hair was washed out with water. Excess water was scraped off each strand of hair.

Subsequently, the hair strands were each dipped in the agent (b) and left in it for 1 minute. Afterwards, excess agent (b) was stripped from each strand of hair. Then, each hair strand was thoroughly washed (1 minute) with water, dried, and visually evaluated.

3. Determination of the Rubbing Fastness

To determine the rub fastness, each strand of hair was combed through 100 times using a comb with fine tines. After that, each strand was visually evaluated again.

| For e.g.: | 1 Comparison | 2 Present disclosure |
|---|---|---|
| Agent (a1) | (a1V) 5.0 g | (a1E) 5.0 g |
| Agent (a2) | (a2) 95.0 g | (a2) 95.0 g |
| Agent (b) | (b) | (b) |
| Coloring before combing | blue ++ uniform coloring | blue +++ uniform coloring |
| Coloring after combing | blue + spotty, uneven | blue ++ uniform coloring |

Color intensity:
− = uncolored
+ = low
++ = average
+++ = particularly good

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material comprising the steps of:
applying an agent (a) to the keratinous material, wherein the agent (a) comprises at least one organic silicon compound from the group of silanes with one, two or three silicon atoms, and wherein the agent (a) further comprises at least one silicone polymer, and
applying an agent (b) to the keratinous material, wherein the agent (b) comprises at least one pigment, wherein the agent (a)—based on the total weight of agent (a)—comprises:
about 0.5 to about 3.0 weight % of at least one first organic silicon compound selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and (2-dimethylaminoethyl)triethoxysilane, and
about 3.2 to about 10.0% by weight of at least one second organic silicon compound selected from the group of methyltrimethoxysilane, methyltriethoxysilane, ethyltrimethoxysilane, ethyltriethoxysilane, octyltrimethoxysilane, octyltriethoxysilane, dodecyltrimethoxysilane and dodecyltriethoxysilane.

2. The process according to claim 1, wherein the agent (a) comprises at least one amino-functionalized silicone polymer.

3. The process according to claim 2, wherein the agent (a) comprises the at least one amino-functionalized silicone polymer comprising structural units of the formula (Si-VI) and of the formula (Si-VII)

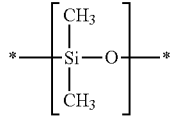

(Si-VI)

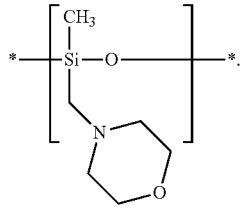

(Si-VII)

4. The process according to claim 1, wherein the agent (a) comprises—based on the total weight of the agent (a)—one or more silicone polymers in a total amount of from about 0.1 to about 8.0% by weight.

5. The process according to claim 1, wherein the agent (b) comprises the at least one inorganic pigment selected from the group of colored metal oxides, metal hydroxides, metal oxide hydrates, silicates, metal sulfides, complex metal cyanides, metal sulfates, bronze pigments and/or colored pigments based on mica or mica coated with at least one metal oxide and/or one metal oxychloride.

6. The process according to claim 1, wherein the agent (b) comprises the at least one organic pigment selected from the group of carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

7. The process according to claim 1, wherein the agent (b) further comprises at least one film-forming, hydrophobic polymer.

8. The process according to claim 1, wherein applying the agent (b) occurs subsequent to applying the agent (a) in which a period between the applications of the agents (a) and (b) does not exceed about 24 hours.

9. The process according to claim 1, comprising the steps in the order indicated of:
(1) applying the agent (a) on the keratinous material,
(2) allowing the agent (a) to act for a period of about 10 seconds to about 10 minutes,
(3) optionally rinsing the keratinous material with water,
(4) applying the agent (b) on the keratinous material,
(5) allowing the agent (b) to act for a period of about 30 seconds to about 30 minutes, and
(6) rinsing the keratinous material with water.

10. A kit-of-parts for dyeing keratinous material, comprising separately packaged:
a first container comprising an agent (a), wherein the agent (a) comprises at least one organic silicon compound selected from the group of silanes having one, two or three silicon atoms, and wherein the agent (a) further comprises at least one silicone polymer, and
a second container comprising an agent (b), wherein the agent (b) comprises at least one pigment, wherein the agent (a)—based on the total weight of agent (a)—comprises:
about 0.5 to about 3.0 weight % of at least one first organic silicon compound selected from the group of (3-aminopropyl)trimethoxysilane, (3-aminopropyl) triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and (2-dimethylaminoethyl)triethoxysilane, and
about 3.2 to about 10.0% by weight of at least one second organic silicon compound selected from the group of methyltrimethoxysilane, methyltriethoxysilane, ethyltrimethoxysilane, ethyltriethoxysilane, octyltrimethoxysilane, octyltriethoxysilane, dodecyltrimethoxysilane and dodecyltriethoxysilane.

* * * * *

UNITED STATES PATENT AND TRADEMARK OFFICE
CERTIFICATE OF CORRECTION

PATENT NO. : 11,564,876 B2
APPLICATION NO. : 17/267655
DATED : January 31, 2023
INVENTOR(S) : Torsten Lechner et al.

It is certified that error appears in the above-identified patent and that said Letters Patent is hereby corrected as shown below:

In the Specification

Column 4, Line 28 change "$C_i$–$C_4$" to --$C_1$-$C_4$--.
Column 5, Line 25 change "R', R' and R''''" to --R', R'' and R'''--.
Column 6, Line 1 change "$R_7$ and $R_5$" to --$R_7$ and $R_8$--.
Column 9, Line 15 change "[O-(A'')]$_{g''}$" to --[O-(A'')]$_g$--.
Column 9, Line 52 change "(Ha)" to --(IIa)--.
Column 9, Line 59 change "[$NR_2$-(A')]" to --[$NR_7$-(A')]--.
Column 18, Line 43 change "R'HZ" to --$R^1$HZ--.

Signed and Sealed this
Thirtieth Day of July, 2024

Katherine Kelly Vidal
*Director of the United States Patent and Trademark Office*